United States Patent [19]

Uchida

[11] Patent Number: 5,424,300
[45] Date of Patent: Jun. 13, 1995

[54] METHOD FOR TREATMENT OF CHRONIC FATIGUE SYNDROME

[75] Inventor: Atsushi Uchida, Uji, Japan

[73] Assignee: Kaken Pharmaceutical Co., Tokyo, Japan

[21] Appl. No.: 135,347

[22] Filed: Oct. 13, 1993

Related U.S. Application Data

[62] Division of Ser. No. 933,092, Aug. 21, 1992, abandoned.

[30] Foreign Application Priority Data

Mar. 18, 1992 [JP] Japan .................................. 4-92158

[51] Int. Cl.⁶ .................... A61K 31/70; A61K 31/715
[52] U.S. Cl. ........................................ 514/54; 514/23;
   514/885; 536/114; 536/118; 536/122;
   536/123.12; 426/800; 426/810
[58] Field of Search ................ 514/885, 23, 54;
   536/118, 122, 123.12, 114; 426/800, 810

[56] References Cited

U.S. PATENT DOCUMENTS

| | | | |
|---|---|---|---|
| 3,819,480 | 6/1974 | Hochschild | 195/1.8 |
| 4,281,009 | 7/1981 | Konishi | 548/309 |
| 5,013,739 | 5/1991 | Bihari et al. | 514/282 |
| 5,055,296 | 10/1991 | Wagle et al. | 514/21 |
| 5,118,673 | 6/1992 | Carpenter et al. | 514/54 |
| 5,126,376 | 6/1992 | Herman | 514/969 |
| 5,155,032 | 10/1992 | Tanaka et al. | 536/1.11 |
| 5,162,037 | 11/1992 | Whitson-Fischman | 600/12 |
| 5,189,022 | 2/1993 | Bridge et al. | 514/16 |
| 5,236,709 | 8/1993 | Soma et al. | 424/195.1 |

FOREIGN PATENT DOCUMENTS 175667 3/1986 European Pat. Off. .
384798 8/1990 European Pat. Off. .

OTHER PUBLICATIONS

Elisabeth Keiffer "The Illness You Can't Sleep Off", Woman's Day, Mar. 1, 1990, pp. 26,30,31 and 32.

Karen Garloch "Lab Test Pinpoints Chronic Fatigue", The Charlotte Observer, Monday, Nov. 19, 1990, pp. 1A and 7A.

Andrew Lloyd et al, "A Double-Blind, Placebo-Controlled Trial of Intravenous Immunoglobulin Therapy in Patients with Chronic Fatigue Syndrome." The American Journal of Medicine, vol. 89, Nov. 1990, pp. 561–568.

Lien, "Fungal Metabolites and Chinese Herbal Medicine as Immunostimulants," Prog. Drug. Res., vol. 34, pp. 395–420 (1990).

G. Chihara et al, "Current Status and Perspectives of Immunomodulators of Microbial Orign", Int. J. Tiss. Reac. IV (3) 207–225 (1982).

*Primary Examiner*—Ronald W. Griffin
*Attorney, Agent, or Firm*—Oblon, Spivak, McClelland, Maier & Neustadt

[57] ABSTRACT

An agent for treatment of chronic fatigue syndrome, which comprises a polysaccharide having a β-1,3-glucoside bond in the main chain as an effective ingredient.

7 Claims, No Drawings

METHOD FOR TREATMENT OF CHRONIC FATIGUE SYNDROME

This is a division, of application Ser. No. 07/933,092, filed on Aug. 21, 1992, now abandoned.

BACKGROUND OF THE INVENTION

1. Field of the Invention

The present invention relates to an agent for treating chronic fatigue syndrome, which comprises a polysaccharide having a β-1,3-glucoside bond in the main chain as an effective ingredient.

2. DISCUSSION OF BACKGROUND

Chronic fatigue syndrome is a disorder characterized by new onset of debilitating fatigue or exhaustion lasting longer than 6 months associated with chronic or recurrent low-grade fever, pharyngitis, lymphadenopathy, myalgia, arthralgia, sleep disorders, as well as neuropsychologic complaints such as difficulties in cognition and temperament and confusion. The Centers for Disease Control (hereinafter referred to as CDC) in U.S.A. have published an epidemiological case definition for chronic fatigue syndrome, which uses major and minor clinical and laboratory criteria. Case Definition for the Chronic Fatigue Syndrome A case of the chronic fatigue syndrome must fulfill major criteria 1 and 2, and the following minor criteria: 6 or more of the 11 symptom criteria and 2 or more of the 3 physical criteria; or 8 or more of the 11 symptom criteria.

MAJOR CRITERIA

1. New onset of persistent or relapsing, debilitating fatigue or easy fatigability in a person who has no previous history of similar symptoms, that does not resolve with bedrest, and that is severe enough to reduce or impair average daily activity level below 50% of the patient's premorbid activity level for a period of at least 6 months.
2. Other clinical conditions that may produce similar symptoms must be excluded by thorough evaluation, based on history, physical examination, and appropriate laboratory findings. These conditions include malignancy; autoimmune disease; localized infection; chronic or subacute bacterial disease, fungal disease, and parasitic disease; disease related to human immunodeficiency virus (HIV) infection; chronic psychiatric disease, either newly diagnosed or by history; chronic inflammatory disease; neuromuscular disease or endocrine disease; drug dependency or abuse; side effects of a chronic medication or other toxic agent; or other known or defined chronic pulmonary, cardiac, gastrointestinal, hepatic, renal, or hematological disease.

Specific laboratory tests or clinical measurements are not required to satisfy the definition of the chronic fatigue syndrome, but the recommended evaluation includes serial weight measurements; serial morning and afternoon temperature measurement; complete blood count and differential; serum electrolytes; glucose; creatinine, blood urea nitrogen; calcium, phosphorus, total bilirubin, alkaline phosphatase, serum aspartate aminotransferase, serum alanine aminotransferase; creatine phosphokinase or aldolase; urinalysis; posteroanteior and lateral chest roentgenograms; detailed personal and family psychiatric history; erythrocyte sedimentation rate; antinuclear antibody; thyroid stimulating hormone level; HIV antibody measurement; and intermediate-strength purified protein derivative (PPD) skin test with controls.

If no such conditions are detected by a reasonable evaluation, this criterion is satisfied.

MINOR CRITERIA

Symptom Criteria

To fulfill a symptom criterion, a symptom must have begun at or after the time of onset of increased fatigability, and must have persisted or recurred over a period of at least 6 months (individual symptoms may or may not have occurred simultaneously). Symptoms include:

1. Mild fever-oral temperature between 37.5° C. and 38.6° C., if measured by the patient-or chills. (Note: oral temperatures of greater than 38.6° C. are less compatible with chronic fatigue syndrome and should prompt studies for other causes of illness).
2. Sore throat.
3. Painful lymph nodes in the anterior or posterior cervical or axillary distribution.
4. Unexplained generalized muscle weakness.
5. Muscle discomfort or myalgia.
6. Prolonged (24 hours or longer) generalized fatigue after levels of exercise that would have been easily tolerated in the patient's premorbid state.
7. Generalized headaches (of a type, severity, or pattern that is different from headaches the patient may have had in the premorbid state).
8. Migratory arthralgia without joint swelling or redness.
9. Neuropsychologic complaints (one or more of the following: photophobia, transient visual scotomata, forgetfulness, excessive irritability, confusion, difficulty thinking, inability to concentrate, depression).
10. Sleep disturbance (hypersomnia or insomnia).
11. Description of the main symptom complex as initially developing over a few hours to a few days (this is not a true symptom, but may be considered as equivalent to the above symptoms in meeting the requirements of the case definition).

Physical Criteria

Physical criteria must be documented by a physician on at least two occasions, at least 1 month apart.

1. Low-grade fever-oral temperature between 37.6° C. and 38.6° C., or rectal temperature between 37.8° C. and 38.8° C.
2. Nonexudative pharyngitis.
3. Palpable or tender anterior or posterior cervical or axillary lymph nodes.

Various criteria other than the above-mentioned criteria have been proposed, but new criteria may be established in compliance with the development of study.

The cause of the cronic fatigue syndrome is not clear as present, and no effective treatment has been established.

SUMMARY OF THE INVENTION

The present inventor has discovered that a polysaccharide having a β-1,3-glucoside bond in the main chain is effective in treating patients with chronic fatigue syndrome, and the present invention has been achieved on the basis of this discovery.

Thus, the present invention provides an agent for treatment of chronic fatigue syndrome, which comprises a polysaccharide having a β-1,3-glucoside bond in the main chain as an effective ingredient.

DETAILED DESCRIPTION OF THE INVENTION

A polysaccharide having a β-1,3-glucoside bond in the main chain used in the present invention may also have a 1,2-, 1,4- or 1,6-glucoside bond in a part and/or branched part of the chain, and these polysaccharides may be a homopolysaccharide comprising the same monosaccharides, a heteropolysaccharide comprising various different saccharides or a complex polysaccharide bonded with a substance other than a saccharide. Examples of these polysaccharide include sizofiran produced by *Schizophyllum commune* Fries, lentinan produced by *Lentinus edodes*, pachyman produced by *Poria cocos*, pachmaran produced by chemically modifying pachyman, paramylon produced by *Euglena gracilis*, leucosin produced by *Phylum crysophyta*, xylan and dulxylan produced by seaweeds such as Canlerpa sp. and *Bryopsis maxima*, curdlan produced by *Alcaligenes faecalis* and succinoglucan as well as sclerotan, scleroglucan, xanthan gum, laminaran, pendulan and the like. Among these polysaccharides, sizofiran and lentinan are particularly preferable.

Sizofiran can be produced by extracellularly by culturing *Schizophyllum commune* Fries, but it is hardly purified because of its highly viscous and thixotropic properties. It is therefore preferable to lower its molecular weight without changing the basic structure of the polysaccharide. Examples of the method for lowering the molecular weight includes ultrasonic treatment and high-shear treatment of a liquor containing sizofiran. The molecular weight is preferably lower than 1,000 kDa, and Sonifilan (registered trademark, a liquid preparation containing 20 mg of sizofiran having an average molecular weight of 450 kDa) known as a sizofiran preparation for an antitumor agent may also be used.

Sizofiran can be used in the form of pulverized mycellium of the sizofiran-producing fungus, i.e. *Schizophyllum commune* Fries.

The agent for treating chronic fatigue syndrome in the present invention can be prepared in accordance with general pharmaceutical preparation techniques in various forms of liquid preparations, syrups, tablets, capsules, powders and granules which can be orally administered, and also in forms of injections, suppositories and aerosols which can be non-orally administered. The agent of the present invention can also be used in combination with other therapeutic regimens.

The dose of sizofiran administered varies depending on symptoms, ages, administration routes, preparation forms or the like. In the case of an ordinary oral administration to an adult, the aimed effect can be achieved by administrating the agent generally in an amount of from 0.5 to 1,000 mg per day in one time or several times. In some cases, it is possible to administer the agent in an amount of 1,000 mg of more.

The treating agent of the present invention can also be administered for prevention of relapse after recovery or for a general preventive purpose.

EXAMPLES

The present invention will be described in further detail with reference to Clinical examples. However, it should be understood that the present invention is by no means restricted to such specific examples.

CLINICAL CASE 1
Patient: A 25 year-old female
Diagnosis: Chronic fatigue syndrome
Chief complaints: Persistent debilitating fatigue, easy fatigability, and low-grade fever
Past history: Nothing particular
Present illness: Twenty months ago, the patient suddenly had low-grade fever, cervical lymph node pain and swelling, and sore throat, followed by debilitating fatigue chills, myalgia, prolonged generalized fatigue after levels of usual working, generalized headaches, migratory arthralgia, inability to concentrate and hypersomnia, thereby more than 50% of her daily activity being impaired. These symptoms continued more than 10 months, and she was frequently suspended from office. She consulted several physicians, resulting in no definitive diagnosis. While she had been treated with vitamin preparations, anti-inflammatory agents and the like, she obtained no clinical benefit from the treatment and finally had to resign from the company.
Physical examination report: Low-grade fever (~38.6° C.), nonexudative pharyngitis, and cervical lymphadenopathy were noted.
Laboratory report: There was nothing abnormal to be specially mentioned.
Treatment: Other clinical conditions that may produce symptoms similar to that associated with chronic fatigue syndrome were excluded, and she was diagnosed as having chronic fatigue syndrome according to the criteria of CDC. Thereafter, she received daily oral administration of a liquid preparation containing 20 mg of sizofiran having an average molecular weight of 450 kDa (hereafter referred to as SPG). Two weeks after the initiation of the SPG therapy, debilitating fatigue and other associated symptoms including low-grade fever, sore throat and inability to concentrate disappeared, and lymphadenopathy, myalgia, prolonged generalized fatigue after levels of usual working, headaches and migratory arthralgia reduced significantly. Hypersomnia was also somewhat cured. She recovered completely from the syndrome except hypersomnia at 6 week point, and the administration of SPG was discontinued at 8 weeks. Thereafter, the patient were completely free from all symptoms and recovered to such a degree as to enjoy exercising at a sport club without any relapse. No side effect was recorded.

CLINICAL CASE 2
Patient: A 19 year-old female
Diagnosis: Chronic fatigue syndrome
Chief complaints: Persistent debilitating fatigue, low-grade fever and insomnia
Past history: Nothing particular
Present illness: Twenty-one months ago, the patient suddenly had flu-like symptoms including low-grade fever, chills, sore throat, cervical and axillary lymph nodes pain and swelling, muscle discomfort, generalized headaches, migratory arthralgia, followed by debilitating fatigue, prolonged generalized fatigue after levels of usual working, inability to concentrate, difficulty in thinking, confusion and insomnia. Since these symptoms became worse, she was suspended from office to see her physical conditions, resulting in no improvement. She consulted a number of physicians and were treated with vitamin preparations, tranquilizers, anti-inflammatory agents, anti-depressants and the like, which produced no clinical benefit. These troublesome conditions lasted for more than 8 months, and she had to finally resign from the company.

Physical examination report: Low-grade fever (38.0° C.), pharyngitis, and cervical lymph node swelling and tender.

Laboratory report: No abnormal findings were recorded.

Treatment: Since other clinical conditions that may produce chronic fatigue syndrome-like symptoms were excluded, she was diagnosed as having chronic fatigue syndrome according to the diagnosis criteria of CDC. Since previous treatments were ineffective, she was treated with daily oral administration of 20 mg of SPG. Two weeks after the initiation of the SPG therapy, such symptoms as low-grade fever, sore throat, lymphadenopathy, muscle discomfort, arthralgia, inability to concentrate, prolonged generalized fatigue, and headaches were calmed down or disappeared, and the fatigue and insomnia were also significantly lessened. Since all the symptoms disappeared after the SPG treatment for 4 weeks, the SPG therapy was discontinued. Thereafter, the patient has been free from the syndrome and returned to normal daily life without further treatment. No side effect was recorded.

CLINICAL CASE 3

Patient: A 43 year-old male

Diagnosis: Chronic fatigue syndrome

Chief complains: Persistent debilitating fatigue, low-grade fever and lymph node swelling Past history: Nothing particular Present illness: Five years ago, the patient suddenly had debilitating fatigue, and was troubled with myalgia, muscle discomfort, generalized muscle weakness, low-grade fever, chills, sore throat, pain and swelling of cervical and axillary lymph nodes, prolonged generalized fatigue after levels of exercise, generalized headaches, migratory arthralgia, inability to concentrate, transient visual scotomata, depression and insomnia. While he visited many hospitals to be diagnosed and treated, no definitive diagnosis was formed and a variety of treatments including vitamin preparations, tranquilizers, muscle relaxants, antidepressants, and anti-inflammatory agents were ineffective. Since these troublesome conditions continued for more than 3 years, he was transferred to a section where a less labor is required to see his physical conditions. The symptoms, however, remained unchanged.

Physical examination report: Low-grade fever (~37.5° C.), pharyngitis, and cervical lymph node swelling and tender.

Laboratory report: No abnormal findings were recorded.

Treatment: The patient met the diagnostic criteria of CDC and was diagnosed as having chronic fatigue syndrome. Since the previous treatments produced no clinical benefit, SPG therapy consisting of daily oral administration of 20 mg SPG was started. Two weeks after the initiation of the therapy, such symptoms as low-grade fever, chills, sore throat and inability to concentrate disappeared substantially, and the debilitating fatigue, exhaustion, cervical lymphadenopathy, prolonged recovery from generalized fatigue, arthralgia, headaches, depression and insomnia were slightly cured, whereas the muscle weakness and myalgia remained unchanged. After 4 week's treatment with SPG all the symptoms except muscle discomfort were notably cured, and the SPG therapy was suspended. Eight weeks later, however, sore throat, generalized muscle weakness, cervical lymphadenopathy, inability to concentrate, insomnia and generalized fatigue relapsed, and SPG therapy was started again. Two weeks after the reopening of the therapy, the symptoms except myalgia were substantially lessened or completely disappeared, and the SPG therapy was suspended three weeks later, however, generalized muscle weakness and prolonged generalized fatigue after usual working relapsed again, and myalgia was exaggerated. Accordingly, he received again the SPG therapy, which resulted in reduction of disappearance of the symptoms. Thereafter, the patient has been free from the relapse and enjoyed normally daily life. No side effect was recorded.

CLINICAL CASE 4

Patient: A 44 year-old female

Diagnosis: Chronic fatigue syndrome

Chief complains: Persistent debilitating fatigue, low-grade fever and lymph node swelling Past history: Nothing particular Present illness: One and a half years ago, the patient suddenly had flu-like symptoms such as low-grade fever, chills, sore throat and headaches, followed by debilitating fatigue, myalgia, muscle discomfort, generalized muscle weakness, cervical lymph node pain and swelling, prolonged generalized fatigue, migratory arthralgia, inability to concentrate, forgetfulness, difficulty thinking, depression and insomnia. The symptoms were so severe that she was largely homebound and could not work as a housewife. Since the conditions remained unchanged, she visited a number of hospitals and repeated admission and discharge to desire close examination and treatment of chromic debilitating fatigue. However, she was not given any definitive diagnosis and received no benefits from a variety of treatments including vitamin preparations, minor tranquilizers, anti-inflammatory agents, and antidepressants.

Physical examination report: Low-grade fever (~38.2° C.), pharyngitis, and cervical and axillary lymphadenopathy.

Laboratory report: There was nothing abnormal to be specially mentioned.

Treatment: The patient met the diagnostic criteria of CDC and was diagnosed as having chronic fatigue syndrome. Since none of the previous treatments were effective, she started to receive SPG therapy consisting of daily oral administration of 20 mg SPG. Three weeks after the initiation of the SPG therapy, such symptoms as low-grade fever, headache, arthralgia and insomnia were lessened, whereas sore throat, muscle weakness, myalgia, the above-mentioned neuropsychologic complaints, prolonged fatigue, generalized fatigue and arthralgia remained unchanged. The neuropsychologic complaints were improved at 6 week point of the therapy, and all symptoms except low-grade fever disappeared at 8 weeks. The patient recovered to such a degree as to carry out a daily life, and the SPG therapy was suspended for a while. However, she again suffered from the syndrome and received the additional SPG therapy. By this treatment most of the symptoms disappeared, and she complained only low-grade fever and slight generalized fatigue after exercise. Thereafter, the administration of SPG was reduced to twice a week, and the patient is now free from the syndrome. No side effect was recorded.

As mentioned above, the pharmaceutical agent of the present invention is effective for treating chronic fatigue syndrome, the optimal method of which has not thoroughly been established yet. The agent of the present invention can be safely used in patients with chronic fatigue syndrome without causing any side effect.

What is claimed is:

1. A method for the treatment of chronic fatigue syndrome, comprising:

administering to a subject in need thereof, an effective amount of a polysaccharide having a $\beta$-1,3-glucoside bond in a main chain of the polysaccharide, in a suitable carrier.

2. The method of claim 1, wherein said polysaccharide further contains a 1,2-, 1,4-, or 1,6-glucoside bond or a combination thereof in a portion of said main chain or in a branched part of said main chain.

3. The method of claim 1, wherein said polysaccharide is selected from the group consisting of homopolysaccharides, heteropolysaccharides and complex polysaccharides wherein a saccharide is bonded with a substance other than a saccharide.

4. The method of claim 1, wherein said polysaccharide is a member selected from the group consisting of sizofiran, lentinan, pachyman, pachmaran, paramylon, leucosin, xylan, dulxylan, curdlan, succinoglucan, sclerotan, scleroglucan, xanthan gum, laminaran and pendulan.

5. The method of claim 4, wherein said polysaccharide is sizofiran.

6. The method of claim 4, wherein said polysaccharide is lentinan.

7. The method of claim 4, wherein said polysaccharide is curdlan.

* * * * *

UNITED STATES PATENT AND TRADEMARK OFFICE
CERTIFICATE OF CORRECTION

PATENT NO.  : 5,424,300
DATED       : June 13, 1995
INVENTOR(S) : Atsushi UCHIDA It is certified that error appears in the above-indentified patent and that said Letters Patent is hereby corrected as shown below:

On the title page, Item [73], the Assignee should read:

--Kaken Pharmaceutical Co., Ltd., Tokyo, Japan--

Signed and Sealed this

Twenty-second Day of August, 1995

Attest:

BRUCE LEHMAN

*Attesting Officer*            *Commissioner of Patents and Trademarks*